United States Patent [19]
Fleischhaker, Jr. et al.

[11] Patent Number: 5,282,478
[45] Date of Patent: Feb. 1, 1994

[54] GUIDEWIRE EXTENSION SYSTEM WITH COIL CONNECTORS

[75] Inventors: Joseph F. Fleischhaker, Jr., Mound, Minn.; Sheryl Higgins, Silverado, Calif.; Michael C. Schiffer, Laguna Hills,, Calif.; Scott Evans, Tustin, Calif.

[73] Assignees: Baxter International, Inc., Deerfield, Ill.; Lake Region Manufacturing Co., Inc., Chaska, Minn.

[21] Appl. No.: 748,301

[22] Filed: Aug. 21, 1991

[51] Int. Cl.$^5$ .............................................. A61B 5/00
[52] U.S. Cl. ..................................... 128/772; 403/229
[58] Field of Search ............... 128/657, 772; 604/95, 604/164, 283; 403/229; 343/715

[56] References Cited

U.S. PATENT DOCUMENTS

| | | | |
|---|---|---|---|
| 2,450,519 | 10/1948 | Luther | 403/229 |
| 2,554,708 | 5/1951 | Kosten | 403/229 |
| 2,751,911 | 6/1956 | Held | 604/283 |
| 2,808,503 | 10/1957 | Ball | 403/229 |
| 2,945,714 | 7/1960 | Egger | 403/229 |
| 3,484,121 | 12/1969 | Quinton | 604/283 |
| 3,631,848 | 1/1972 | Muller | 604/95 |
| 3,906,938 | 9/1975 | Fleischhaker . | |
| 4,538,622 | 9/1985 | Samson et al. | 128/772 |
| 4,719,924 | 1/1988 | Crittenden et al. | 128/772 |
| 4,827,941 | 5/1989 | Taylor et al. | 604/164 |
| 4,846,193 | 7/1989 | Tremulis et al. | 128/772 |
| 4,875,489 | 10/1989 | Messner et al. | 604/164 |
| 4,886,500 | 12/1989 | Lazarus | 604/164 |
| 4,895,168 | 1/1990 | Machek | 128/772 |
| 4,907,332 | 3/1990 | Christain et al. | 29/237 |
| 4,917,103 | 4/1990 | Gambale et al. | 128/657 |
| 4,922,923 | 5/1990 | Gambale et al. | 128/772 |
| 4,934,380 | 7/1990 | de Toledo | 128/772 |
| 4,966,163 | 10/1990 | Kraus et al. | 128/772 |
| 5,002,560 | 3/1991 | Machold et al. | 604/95 |
| 5,101,213 | 3/1992 | Harada et al. | 343/715 |
| 5,113,872 | 5/1992 | Jahrmarkt et al. | 128/772 |
| 5,117,838 | 6/1992 | Palmer et al. | 128/772 |

FOREIGN PATENT DOCUMENTS

| | | |
|---|---|---|
| 0347035 | 12/1989 | European Pat. Off. . |
| 0367472 | 5/1990 | European Pat. Off. . |
| 0380227 | 8/1990 | European Pat. Off. . |
| 383159 | 8/1990 | European Pat. Off. . |
| 0674943 | 8/1990 | Switzerland ............ 128/772 |
| 2180454 | 4/1987 | United Kingdom . |

OTHER PUBLICATIONS

Hartzler, Rutherford, and McConahay; "Retained Percutaneous Transluminal Coronary Angioplasty Equipment Components and Their Management" American Journal of Cardiology, vol. 60, Dec. 1, 1987; pp. 1260-1264.

Warren, S. G.; Barnett, J. C.; "Catheterization and Cardiovascular Diagnosis", Wiley-Liss, Inc.; vol. 20, No. 3, Jul. 1990, pp. 212-215.

Primary Examiner—Max Hindenburg
Attorney, Agent, or Firm—Grady Frenchick; Debra D. Condino; Raymond Sun

[57] ABSTRACT

An extendable guidewire system including a guidewire and extension wire bearing separate helical coil connectors. The coil connectors, at least in part, have spatially separate adjacent coil turns, thereby providing gaps for receiving coil turns of the other connector.

25 Claims, 5 Drawing Sheets

GUIDEWIRE EXTENSION SYSTEM WITH COIL CONNECTORS

BACKGROUND OF THE INVENTION

The present invention generally relates guidewires used in vascular surgery and procedures, and specifically to angioplasty and embolectomy guidewires.

Guidewires are used in various surgical catheter procedures to steer a catheter to a desired location in the patient's vascular system. Generally, the guidewires are inserted and steered through the patient's vascular system to the desired site. The catheter is typically positioned over a portion of the guidewire during this initial placement, and then pushed along the guidewire until properly positioned at the desired site. Standard guidewires are typically longer than the catheter to allow for independent movement of the catheter and the wire. Examples of suitable guidewires are illustrated in U.S. Pat. No. 4,538,622, issued to Samson et al on Sep. 3, 1985; U.S. Pat. No. 4,719,924, issued to Crittenden et al on Jan. 19, 1988; U.S. Pat. No. 4,934,380, issued to de Toledo on Jun. 19, 1990 and European Patent Application Number 89304257.2, published on Dec. 20, 1989.

In one particular surgical application, angioplasty, the guidewire is steered to the vascular blockage. Usually the steering of the guidewire is facilitated by a video X-ray device allowing the surgeon to visually observe the movement of the guidewire. The guidewire usually includes a radiopaque marker at its distal end to provide a reference for the surgeon. The surgeon positions the radiopaque marker adjacent the blockage, and then slides a balloon angioplasty catheter over the wire to the blockage.

Generally the balloon is expanded to open the blockage and then is removed along with the guidewire. However, sometimes the balloon breaks, or a larger sized balloon is required to fully open the blockage. In either situation the balloon catheter must be removed, and a replacement catheter is slid over the guidewire.

It is usually desirable to maintain the guidewire in the patient to reduce the time required to reposition the balloon at the blockage. The initial placement of the balloon and wire requires extensive manipulation of the guidewire, and removal and repositioning of the wire is time consuming, and in certain circumstances undesirable.

When required, the surgeon removes the catheter over the guidewire, retaining the wire in the patient. To facilitate the easy removal and replacement of the balloon catheters the guidewire must be sufficiently long enough to allow the surgeon to grip a portion of the wire as the catheter is being withdrawn. This requires the guidewire be long enough to provide an external portion longer than the catheter. However, a wire this long is difficult to steer, and as a result, guidewires are usually only slightly longer than the typical balloon catheter, e.g. 20-50 centimeters.

One previous method used to allow for the exchange of balloon catheters involved replacing the original guidewire with a longer guidewire, and then removing and replacing the catheter. This approach proved to be tedious.

A more recent development involves coupling a length of a second wire to the exposed guidewire end. The second wire length should be sufficient to allow the catheter to be withdrawn while retaining the placement of the guidewire in the patient. Various approaches have been suggested for affecting this coupling action.

United Kingdom Patent Application Number 8615949, published Apr. 1, 1987, corresponding to U.S. Pat. No. 4,917,103, issued to Gamble et al on Apr. 17, 1990, discloses a guidewire extension wire with a tubular connector fitted to the end of either the exposed guidewire or the extension wire. The other wire is formed with a reduced diameter end which slips into the tubular connector. To enhance the fit, Gamble et al discloses crimping the tubular connector. The basic disadvantage to this approach is that the tubular connector does not sufficiently grip the reduced diameter end of the wire unless crimped to prevent dislodging of the guidewire from the extension during the catheter exchange. Crimping of the tubular connector is not reversible requiring the extension wire to be cut off the guidewire exposed end. U.S. Pat. No. 4,922,923, also issued to Gamble on May 8, 1990, teaches the method of connecting the guidewire and extension wire with the described tubular connector.

A variation of the Gamble et al approach is disclosed in U.S. Pat. No. 4,827,941, issued to Taylor et al on May 9, 1989. Again an extension wire is affixed to the exposed proximal end of the guidewire using a tubular connector affixed to the end of either the guidewire or the extension wire. However, the mating end of the guidewire or extension wire is formed to frictionally engage the interior of the tubular connector. This is accomplished by providing the mating end as an undulating smaller diameter segment. While this approach overcomes the need to crimp the tubular connector, there remains the potential of disengagement between the tubular connector and the undulating segment during the catheter exchange procedure.

A modification to the friction approach suggested by Taylor et al is disclosed in U.S. Pat. No. 4,875,489, issued to Messner et al on Oct. 24, 1989. Messner et al discloses the use of two coaxially tubular connectors mounted at either the guidewire proximal end, or the extension wire connecting end. The innermost tubular connector is formed with a longitudinal slot allowing for expansion of the connector diameter as a reduced diameter portion of the other wire is inserted. The outer tubular connector limits the extent of this expansion and reinforces the overall structure. This approach has the disadvantage of disengagement during the catheter exchange procedure.

An approach similar to Messner et al is disclosed in European Patent Application 89304257.2, published on Dec. 20, 1989. In this approach a coil spring is mounted about the reduced diameter portion of either wire. This end is inserted into a tubular connector mounted to the end of the other wire and the insertion into the tubular connection causes at least some of the coil turns to engage in light interference with the internal surface of the tubular connector. This interference longitudinally stretches and constricts the coil, allowing insertion into the tubular connector. Once fully inserted the coil returns to an unconstricted state to grip inside the connector. The main disadvantage of this device is that disengagement requires simultaneous turning and pulling of the connection to compress the spring to enable dislodging from the tubular connector.

U.S. Pat. No. 4,846,193 to William S. Tremulis et al. describes an extendable guidewire which permits the introduction and exchange of catheters. The guidewire of the '193 Tremulis patent has a telescopically mounted inner shaft or wire having axially extended and retracted positions.

Commercially available devices similar to those disclosed in European Patent Application 89304257.2 and Taylor et al possess tubular connectors of larger diameters than the associated wire. One system is the DOC TM Guide Wire Extension by Advanced Cardiovascular Systems, Inc., 26531 Ynez Road, Temecula, Calif. The DOC TM Guide wire extension is similar in design to that described in Taylor et al (U.S. Pat. No. 4,827,941) A second system, the LINX TM Guide Wire Extension by USCI Division of C.R. Bard, Inc., 129 Concord Road, Billerica, Mass. is similar in design to the devices disclosed in the European Patent Application 89304257.2. The larger diameter connector requires that the catheter, which is being passed over the guidewire, possess a larger internal diameter than would be necessary to fit over the smaller diameter guidewire.

The disadvantage of the use of a larger diametered connector is also found with devices made in conformance with Gamble et al, and enhanced when the tubular connector is crimped.

Another worker has suggested the use of female and male threaded body connectors to interconnect the guidewire and extension wire, see U.S. Pat. No. 4,966,163, issued to Kraus et al on Oct. 30, 1990. This device includes an internally threaded female portion in which is fit an externally threaded male portion. A preferred embodiment requires that either the female or male portion be rotatably mounted to the associated wire to allow free rotation. This free rotation assists in the ability to thread the two portions together.

A disadvantage with the Kraus et al device is the fabrication of the female and male threaded sections. The actual size of the connectors is relatively small, i.e. less than 2.3 millimeters. It is difficult to fabricate female and male threaded portions of this size. If the size of the connectors is increased over the diameter of the guidewire and extension wire, the disadvantages discussed above for the DOC TM and LINX TM Guide Wire Extension systems apply.

It is thus apparent that the need remains for a suitable guidewire extension system using an extension wire which is reliably connected to the guidewire without the described disadvantages.

SUMMARY OF THE INVENTION

The present invention overcomes the above discussed disadvantages by providing a guidewire extension system including a guidewire with proximal and distal ends, and an extension wire with opposing ends. First and second flexible connectors are mounted to one of the extension wire ends and the guidewire proximal end. The connectors are interlocking helical coils which are connected by rotating one with respect to the other.

The preferred embodiment of the extendable guidewire system of the invention includes a guidewire section and an extension wire section. The guidewire section is designed for placement into a vascular system and has proximal and distal ends. The guidewire section proximal end includes a helical coil with the most proximally located helical coil turns spatially separated to form gaps between adjacent turns. The extension wire section has a diameter substantially equivalent to that of the guidewire section, and includes at one of its opposing ends a helical coil formed with gaps between adjacent turns. The gaps of the two helical coils are compatibly spaced and adapted to receive the other helical coil turns when the guidewire proximal end helical coil and extension end helical coil are screwed together.

In an even more preferred embodiment, a stem, pilot, or guide pin extends from one or the other of the helical coils. The guide pin is adapted to be received inside the other of the helical coils to enhance ease of interlock. A cooperating tubular sleeve, socket extension or coupling tube may be included within one or the other of the helical coils. The socket extension would cooperate with and receive the guide pin located within the other coil to enhance the ease of coil interlock and connector rigidity.

In another embodiment, the cooperating helical coils are provided with means to enhance or to identify their state of interlock. Specifically, an affirmative lock or snap means may be provided on cooperating segments of the respective coils so that an intended state of interlock may be identified. Alternatively, diminishing or increasing coil separation distance may be utilized to increase or enhance the interaction between coils. Rotation or winding of the coils into each other becomes increasingly difficult as the intended coupling state is approached.

DESCRIPTION OF THE DRAWINGS

The present invention may be better understood and the advantages will become apparent to those skilled in the art by reference to the accompanying drawings, wherein like reference numerals refer to like elements in the several figures, and wherein.

DESCRIPTION OF THE PREFERRED EMBODIMENTS

The present invention is directed to guidewire extension systems useful for various medical procedures, i.e. angioplasty and embolectomy. Guidewires generally include a main core, preferably composed of a solid wire. A helical coil spring is mounted about the distal portion of this core wire. The distal ends of the core wire and helical coil springs may be connected by brazing, adhesive bonding, mechanical interaction, or restriction fit. The proximal portion of the guidewire is usually formed by only the core wire. This proximal portion may be coated with a polymeric material, e.g. polytetrafluoroethylene, to enhance the lubricity of the guidewire. Without limiting the present invention to any particular size, typical guidewire dimensions are from about 100 centimeters (cm) to 400 cm long and from about 0.008 inches to about 0.100 inches in diameter.

The precise construction of a guidewire employed with the present invention is not critical. Many different types of guidewire configuration are suitable. Examples of such guidewires are found in U.S. Pat. No. 4,538,622, issued to Samson et al on Sep. 3, 1985; U.S. Pat. No. 4,719,924, issued to Crittenden et al on Jan. 19, 1988; U.S. Pat. No. 4,934,380, issued to de Toledo on Jun. 19, 1990 and European Patent Application Number 89304257.2, published on Dec. 20, 1989.

The main modification to the described guidewire construction is the provision of a helical coil connector at the very proximal end of the guidewire. This helical coil is coupled with a similarly configured helical coil arranged at one end of an extension wire. Specifically, each helical coil is at least partially loosely wound or stretched to provide gaps between adjacent coil turns. The dimension of these gaps is sufficient to allow the two coils to be easily twisted together, while maintaining a sufficiently positive engagement or interaction therebetween. The positive interaction may be restrictive or frictional, or simply cooperative.

The connection between the two coils has many advantages over the commercially available guidewire extension coupling systems. One possible advantage is that the dual helical coil connector of the present invention remains flexible after connection, as compared to the commercially available systems which incorporate a hypotube as one part of the connector. This connection flexibility may be useful in certain applications.

A further advantage is that the diameter of the dual helical coil connector remains substantially the same as that of the guidewire and extension wire. In comparison, commercially available guidewire extension connectors include a hypo tube which is generally larger in diameter than the guidewire or extension wire. For example, the hypo tube connector used in the DOC TM Guide Wire Extension by Advanced Cardiovascular Systems, Inc., 26531 Ynez Road, Temecula, Calif., and the LINX TM Guide Wire Extension by USCI Division of C.R. Bard, Inc., 129 Concord Road, Billerica, Mass. is slightly larger than the guidewire and extension wire. This slight difference may interfere with the passage of the catheter over the connector, and does limit the types of catheter sizes useful with a particular extension system.

Figures 1, 4:
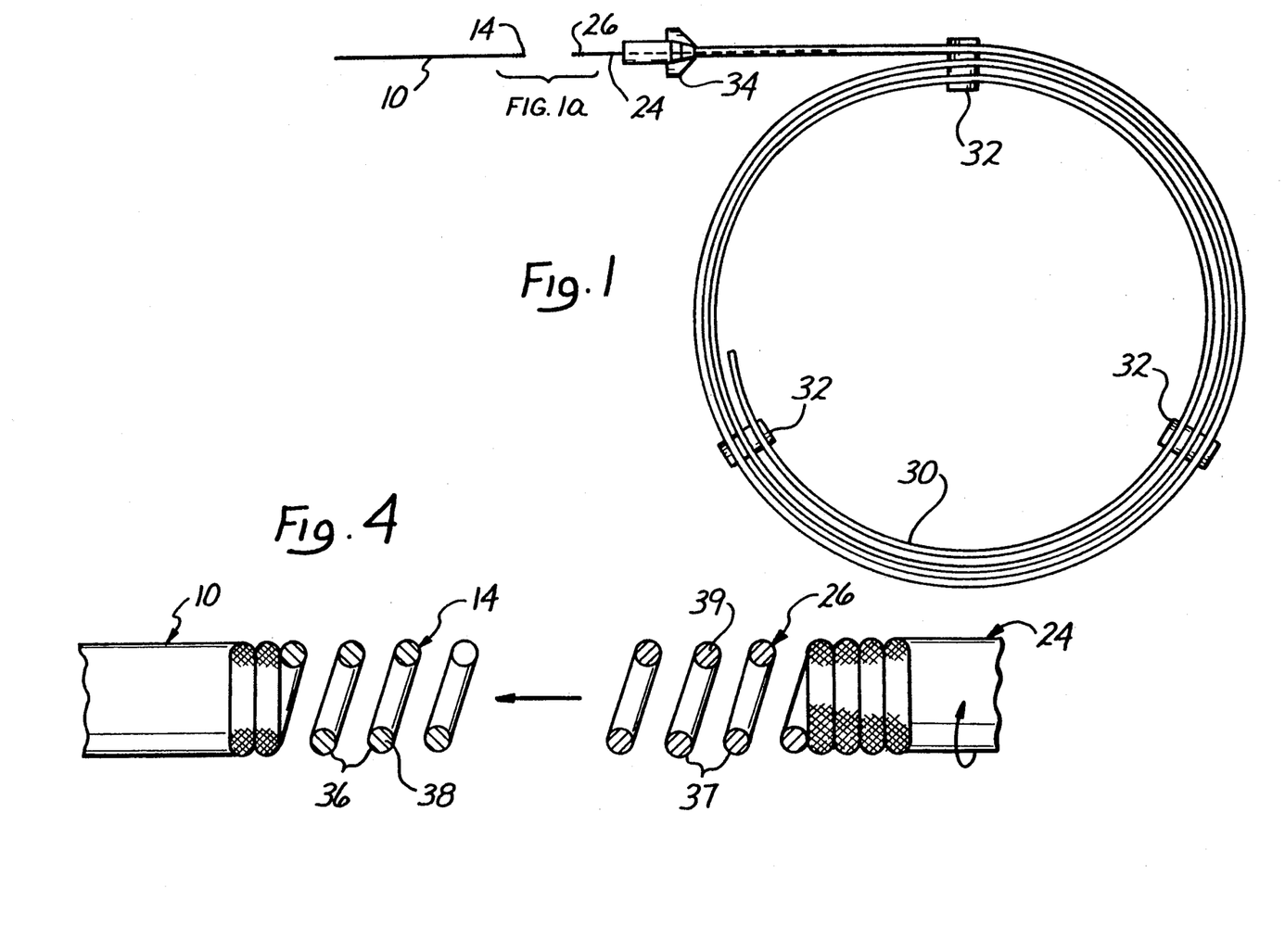
FIG. 1 is a prospective view of a guidewire and an extension wire in accordance with the invention, with the extension wire fitted in a coiled tubular holder.
FIG. 4 is a side view of a further embodiment of the helical coil connectors respectively affixed to the ends of the guidewire and the extension wire.
Figure 1A:
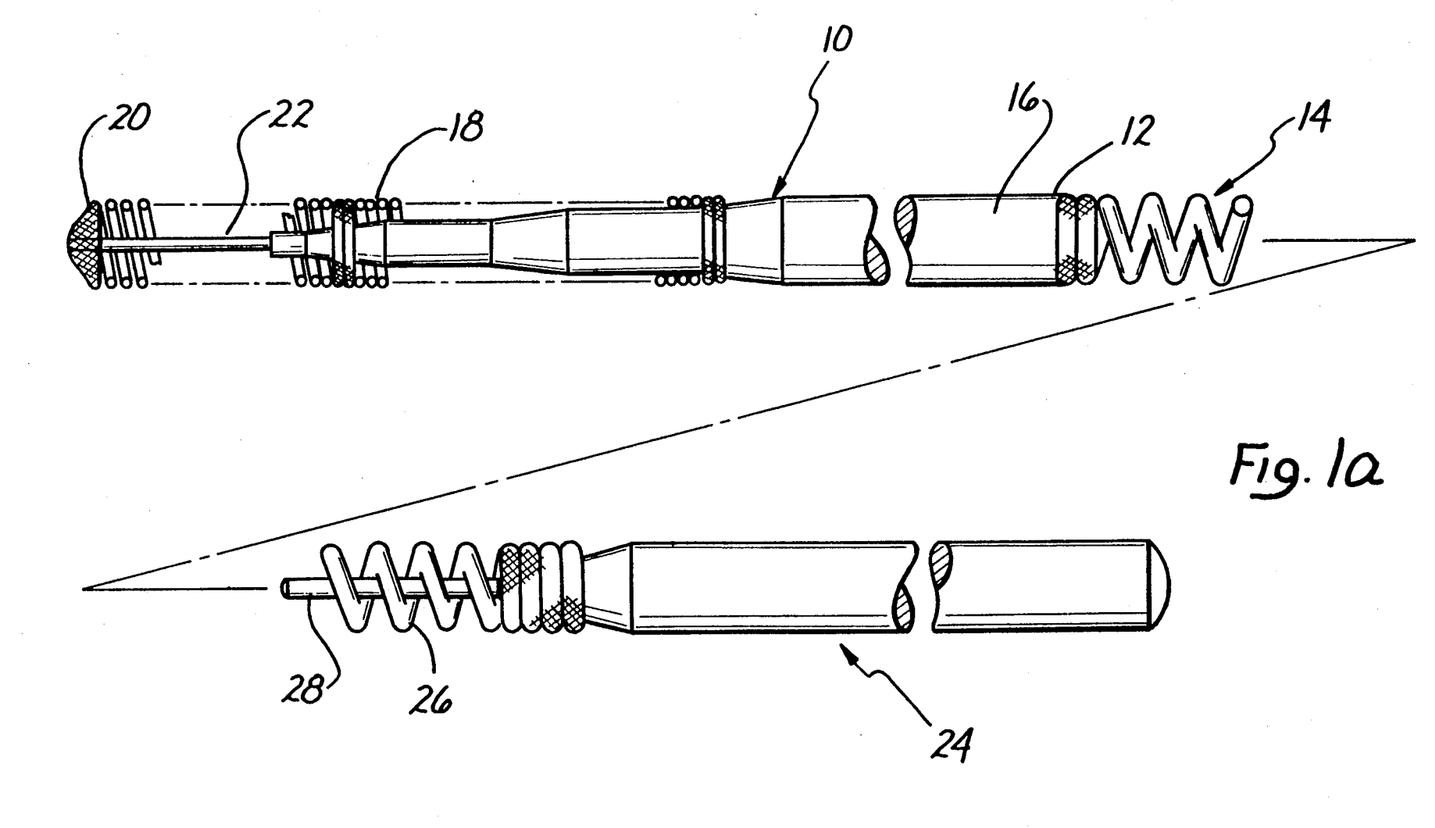
FIG. 1A is a partially sectional enlarged view of the guidewire and extension wire of FIG. 1 at 1A.

A more detailed explanation of the present invention will be described with reference to FIGS. 1 and 1A illustrating a guidewire 10 and an extension wire 24. Guidewire 10 is of standard guidewire construction modified at its proximal end 12 with a helical coil connector 14 in accordance with the invention. The guidewire 10 includes a core wire 16 and a distally located helical coil spring 18. Core wire 16 is tapered at both ends. The core wire 16 and distally located helical coil spring 18 are brazed together at their distal ends, as seen at 20. The distal end of the core wire 16 forms a safety wire 22, whose function is well known. The precise construction of guidewire 10 (other than its proximal end) is not critical to the invention, and will not be described in any further detail herein.

Extension wire 24 is generally formed from an elongated, constant diameter wire provided at one end with a helical coil connector 26. Preferably, as seen better in FIG. 1A, the extension wire 24 end to which the helical coil connector 26 is connected is provided with a guiding pin 28. Guiding pin 28 may be formed by tapering the respective end of extension wire 24, or brazing a pin to such end. Guiding pin 28 is dimensioned to fit inside the distally located helical coil connector 14 of guidewire 10. While guiding pin 28 is shown on the end of extension wire 24, it may be provided on the proximal end 12 of guidewire 10.

It is also preferred to store the extension wire 24 in a tubular shipping container 30, which is held in a spiral configuration, as seen in FIG. 1, by one or more mounting brackets 32. In operation the guidewire 10 will have been previously placed in a patient's vascular system, not shown, with only the proximal end 12 exposed. The extension wire 24 end bearing the helical coil connector 26 is brought into engagement with the helical coil connector 14 of the guidewire 10. Generally, the guiding pin 28 is slipped inside the helical coil connector 14 to align the positioning of the two helical coil connectors 14 and 26.

Once aligned the two helical coil connectors 14 and 26 may be twisted or rotated with respect to each other so that the respective spaced coils helically engage to provide the chosen or predetermined positive engagement. While the extension wire 24 may be turned by hand, a torque device 34 also may be used to facilitate the turning of the extension wire 24. Suitable torque devices are commercially available and generally provide a hub which is mechanically affixed to the extension wire 24. Examples of commercially available torque devices are sold by the USCI Division of C.R. Bard Inc., 129 Concord Road, Billerica, Mass. 01821, under the name "Steering Handle", catalog number 008958, or by Advanced Cardiovascular Systems, Inc., 26531 Ynez Road, Temecula, Calif., 92390, under the name "Torque Device", Catalog Number 22215.

Figure 2A:
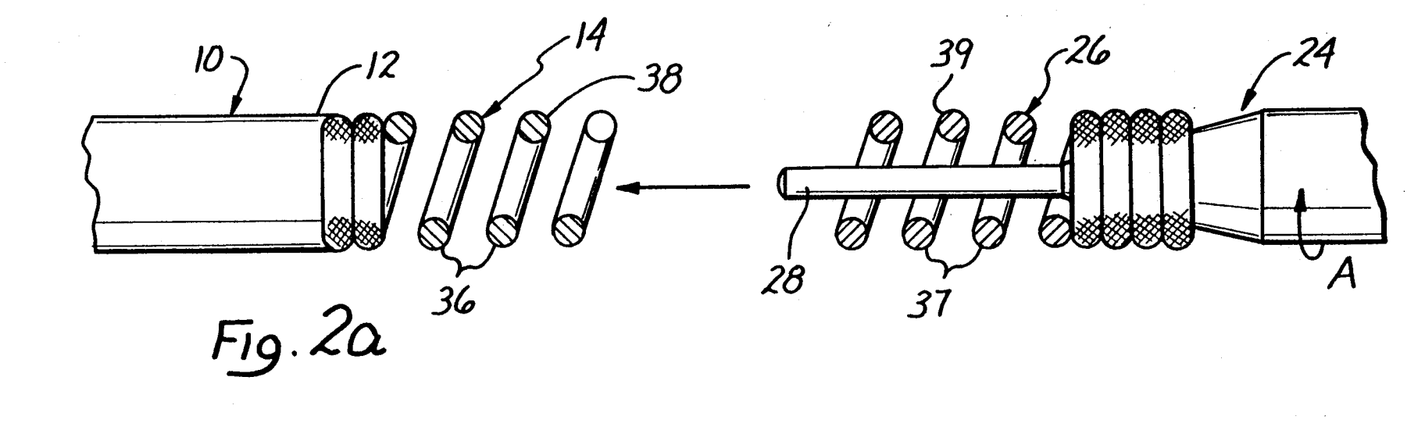
FIGS. 2A and 2B are close-up views of the helical coil connectors before and after coupling.
Figure 2B:
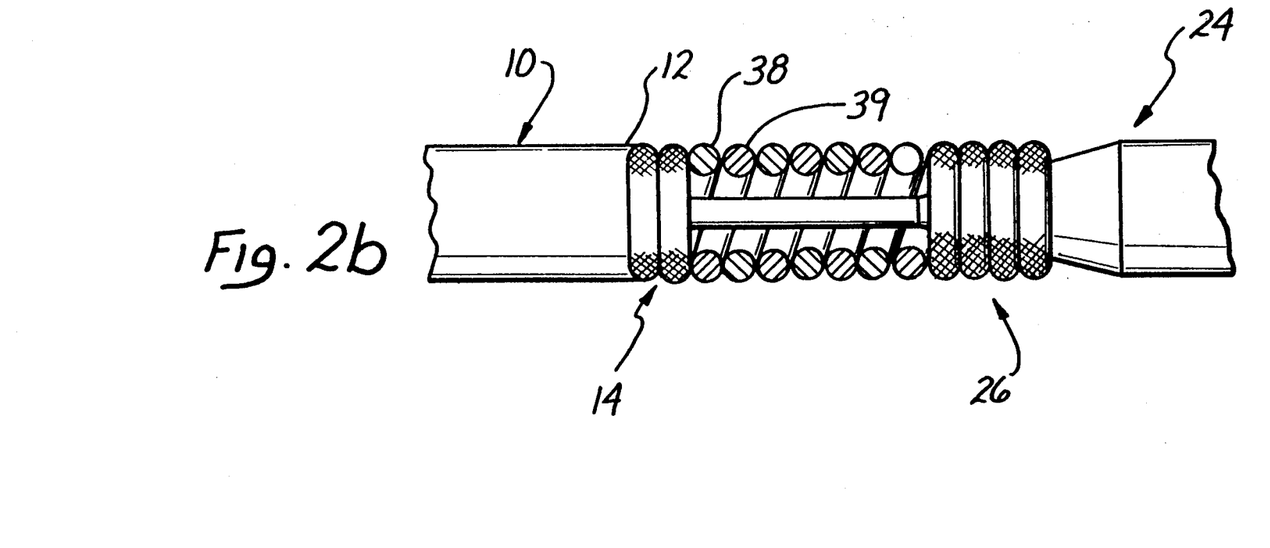

The coupling of the guidewire 10 and extension wire 24 will be described in greater detail with reference to FIGS. 2A and 2B. FIG. 2A illustrates the respective proximal end 12 of guidewire 10, and that end of extension wire 24 bearing the helical coil connector 26. As seen, the helical coil connectors 14 and 26 are formed from helical coil springs which are partially configured with loosely wound (or stretched) turns 38 and 39 respectively that form gaps 36 and 37 between the adjacent coil turns 38 and 39. The size of the gaps 36 and 37 are provided to snugly receive the respective spaced apart coil turns 38 and 39.

In particular, the helical coil connectors 14 and 26 are formed with the spatially separated coil turns 38 and 39. This spatial separation may be formed in any manner, with the distances between adjacent coil turns 38 forming the gaps 36 and 37 being only slightly larger than the diameter of the coil turns 38 and 39. The number of spatially separated coil turns 38 and 39 defining gaps 36 and 37 is not critical to the invention, provided that there is a sufficient number to provide an effective connection between the helical coil connector 14 and the helical coil connector 26.

Alternatively, the spatial separation between coil turns may be varied to enhance their primarily frictional, helical interaction or engagement. Thus, for example, gaps 36, 37 may be reduced adjacent the body of the guidewire so that the leading end segment of extension coil connector 26 is more affirmatively engaged. Coil separation distances for extension coil 26 may be analogously diminished adjacent the extension body to provide the same enhanced frictional engagement with guidewire coil connector 14.

Connection between the helical coil connectors 14 and 26 is performed by inserting the guiding pin 28 into the helical coil connector 14. Rotation, e.g., in the direction of arrow A, causes coil connectors 14 and 26 to be positively and helically engaged. Guiding pin 28 aligns the respective coil turns 38 and 39 of the two connectors 14 an 26 to ensure proper mating or engagement of connectors 14 and 26, as seen in FIG. 2B. Once engaged, the helical coil connectors 14 and 26 form a flexible joint between the guidewire 10 and extension wire 24. In an alternative embodiment of the invention, neither the guidewire 10, nor the extension wire 24 is provided with the guiding pin 28. This embodiment is illustrated in FIG. 4. In this embodiment, the respective helical coil connectors 14 and 26 are aligned without the assistance of a guiding pin 28.

As stated, this flexible joint provides advantages over the joints formed by the commercially available guidewire extension connector systems described above. Furthermore, the connectors 14 and 26 are easily disengaged by twisting or rotating in a direction opposite to that of the coil wind. The connection system of the invention also provides an easily reusable connection in those circumstances where additional replacement catheters are required, for example, when additional balloon catheters are required for one angioplasty procedure.

In a more preferred embodiment, one of the ends of the guidewire 10 or extension wire 24 adjacent the helical coil connectors 14 or 26 includes a rotatable joint. This rotating joint fosters the rotation of the associated helical coil connector during the connection procedure by allowing that portion of the wire carrying the connector to be rotated independently from the remainder of the wire. This feature can be useful, for example, when the guide wire coil and extension wire coil are wound together while the remainder of the extension is fitted in the coiled tubular holder (FIG. 1).

Figures 3A, 3B:
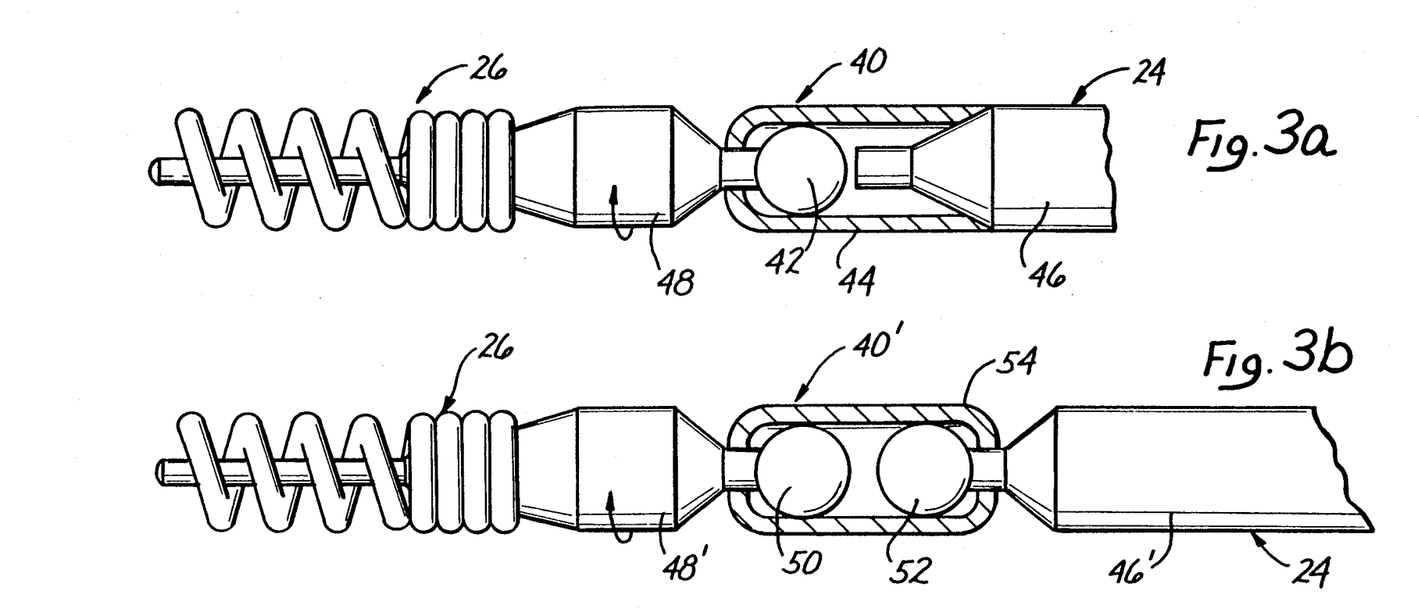
FIG. 3A-C are side views of various embodiments of the invention incorporating rotating joints contiguous the helical coil.
Figure 3C:
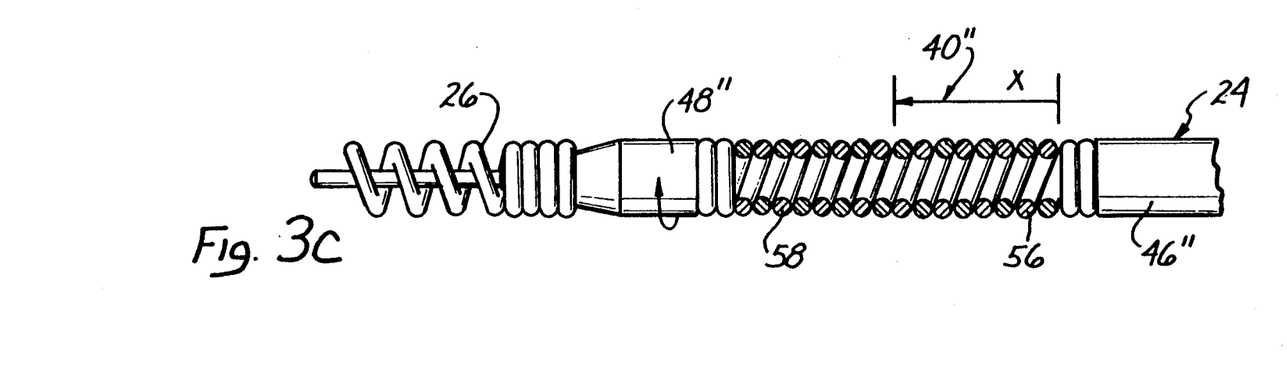

Examples of suitable rotating joints are illustrated in FIGS. 3A-C. While these embodiments will be described with reference to providing the extension wire 24 with the rotating joint, it should be noted that the described rotating joint may be provided at the proximal end 12 of guidewire 10.

One such rotating joint as seen in FIG. 3A at 40 is a ball 42 and socket 44 configuration. In this embodiment, the rotating joint 40 is located on the extension wire 24 at a location contiguous to the helical coil connector 26. Specifically, the end of extension wire 24 is divided into a main portion 46 and a connector portion 48. The connector portion 48 includes one end bearing the helical coil connector 26, with the opposite end formed with the ball 42. The main portion 46 includes one end bearing the socket 44 formed about the ball 42 of the connector portion 48. In this manner the connector portion 48 may be freely rotated with respect to the main portion 46. Connector portion 48 may be gripped and rotated by hand or by means of a torque device discussed above.

An alterative rotating joint of this invention is seen in FIG. 3B. This rotating joint 40' is also located on the extension wire 24 at a location contiguous to the helical coil connector 26. Again, the extension wire 24 is divided into a main portion 46' and a connector portion 48'. The connector portion 48' includes one end bearing the helical coil connector 26, with the opposite end formed with a ball 50. The main portion 46' includes one end bearing a second ball 52. The balls 50 and 52 are rotatably held in a sleeve 54.

A still further embodiment of the rotating joint is seen in FIG. 3C. This embodiment is formed by a second helical coil connector arrangement having a twist direction opposite that of the connector formed from helical coil connectors 14 and 26 shown in FIG. 2A and B. Again, the extension wire 24 is divided into a main portion 46" and a connector portion 48". The main portion 46" includes a first helical coil 56 twisted together with a second helical coil 58 mounted at one end of connector portion 48". The opposite end of the connector portion 48" bears the helical coil connector 26. The total length in which the first helical coil 56 and second helical coil 58 are twisted together should be sufficiently greater than the overall length to which the helical coil connectors 14 and 26 will be screwed together, represented as distance X, to ensure that the main portion 46" and connector portion 48" will not become disengaged.

In another embodiment of the present invention, the connector may be provided with means to identify when the coil connectors 14 and 26 are affirmatively engaged. For example, the coil connectors 14 and 26 could be provided with cooperating dimple-detente means so that when suitably engaged, an affirmative "snap" would be felt or heard. Alternatively, cooperating projections and slots could be provided within or between cooperating segments of coil connectors 14, 26 so that affirmative engagement is identified. Many variations upon this affirmative identification means would be apparent to one of skill in this art.

Figure 5A:
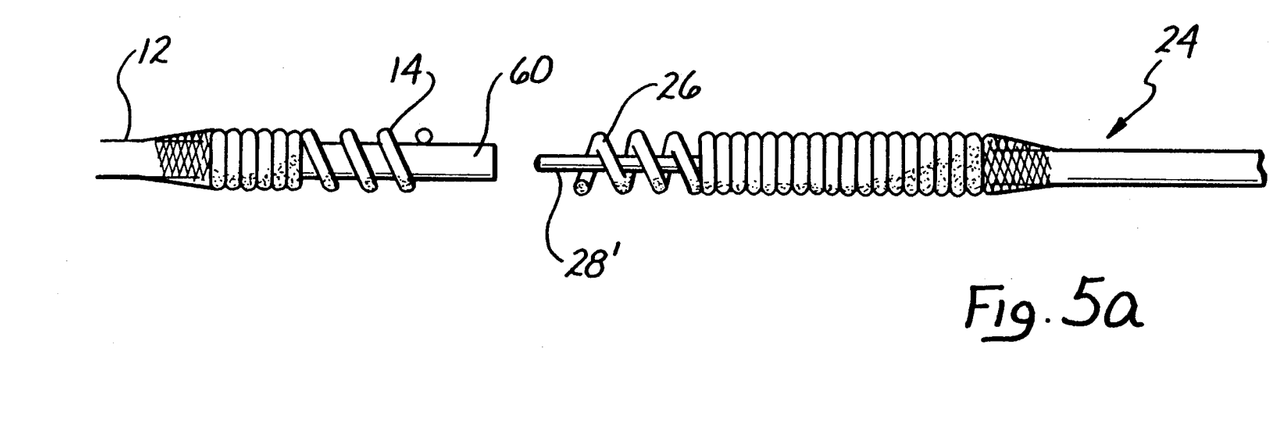
FIGS. 5A and 5B are side view of still further embodiments of the helical coil connectors of the invention.
Figure 5B:
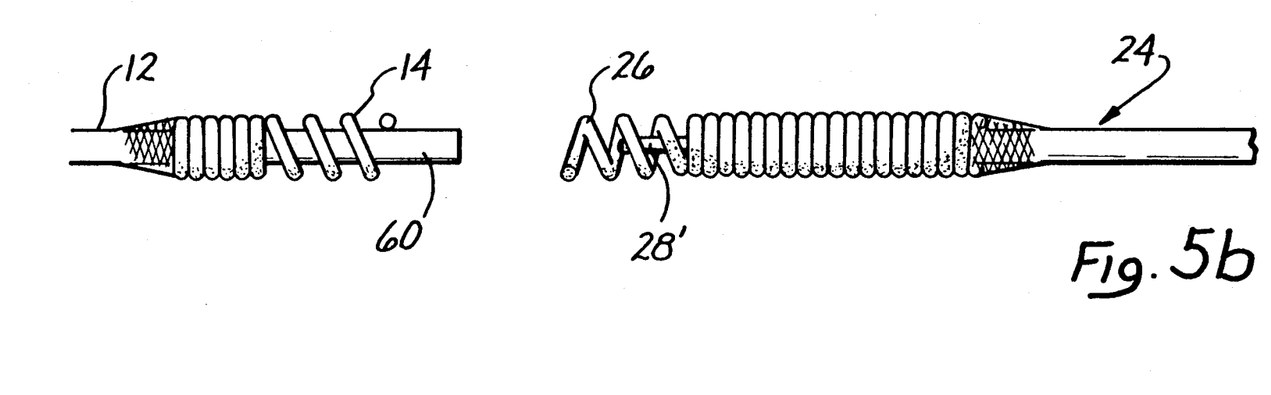

Further embodiments of the invention are seen in FIGS. 5A and 5B. In these embodiments, the helical coil connector not carrying the guiding pin 28 includes a cooperating, tubular, female socket extension 60. Socket extension 60 is dimensioned to receive the guiding pin 28, and assists in aligning the helical coil connector 14 with helical coil connector 26 during the coupling process. Socket extension 60 and helical coil connectors 14 and 26 may be brazed, bonded or machined from the end of either the proximal end of the guide wire 12 or from extension wire 24. The use of the socket extension 60 provides additional stiffness reducing the possibility of kinking of the helical coils during the coupling process.

The primary difference between the embodiments illustrated in FIGS. 5A and 5B are the length of the guiding pin, seen at 28 and 28,' respectively. Guiding pin 28 is seen to extend from the helical coil connector 26 in FIG. 5A, while guiding pin 28' remains within the envelope of the interior of the helical coil connector 26 in FIG. 5B. The length of the socket extension 60 may also be similarly adjusted.

Socket extension 60 may be designed to completely or partially receive guiding pin 28 or 28'. By restricting the progress of guiding pin 28 or 28' into the socket extension 60 the extent of the helical interaction between the helical coil connectors 14 and 26 may be controlled to prevent overturning of the connectors 14 and 26. This limits the possibility of overlapping the coil turns by excessive winding of connectors 14 and 26 with respect to each other. A further modification of the embodiments of FIGS. 5A and 5B involves providing a releasable keeper inside the socket extension 60 for snapping onto the end of the guiding pin 28 for providing a tactile sensation to the user of the device indicating successful coupling of the connectors 14 and 26.

While the preferred embodiments have been described, various modifications and substitutions may be made thereto without departing from the scope of the invention. Accordingly, it is to be understood that the invention has been described by way of illustration and not limitation.

What is claimed is:

1. An extendable guidewire system comprising:
    a guidewire section designed for placement into a vascular system having proximal and distal ends, the guidewire section proximal end including a helical coil having a free end and spaced apart adjacent coil turns; and
    an extension wire with opposing ends with one of such ends including a helical coil having a free end and spaced apart adjacent coil turns, the coil turns of the guidewire proximal end helical coil or the extension wire helical coil being spacially separated so as to receive the coil turns of the other helical coil when the free ends of the guidewire proximal end helical coil and extension end helical coil are rotated into each other.

2. A guidewire system of claim 1 wherein the extension wire section end including the helical coil includes a stem which extends from the helical coil, the stem being adapted to guide the extension wire helical coil into the guidewire section proximal end helical coil.

3. The extendable guidewire system of claim 2 wherein the guidewire section includes a rotating joint contiguous the guidewire section proximal end helical coil.

4. The extendable guidewire system of claim 2 wherein the extension wire section includes a rotating joint contiguous the extension wire section end helical coil.

5. The extendable guidewire system of claim 4 wherein the rotating joint is a ball and socket joint.

6. The extendable guidewire system of claim 4 wherein the rotating joint is formed by a first coil having spatially separated turns and a second coil having spatially separated turns, with the first and second coil spatially separated turns being adaptable to receive the other spatially separated turns in a winding relationship as the guidewire proximal end helical coil and extension wire end helical coil are being rotated together.

7. The extendable guidewire system of claim 2, wherein the guidewire section includes a cylindrical receiver attached to said guidewire and extending out from said helical coil.

8. The extendable guidewire system of claim 1 wherein the coil guidewire section proximal end including the helical coil further includes a stem extending from the helical coil, the stem being adapted to guide the guidewire helical coil into the extension wire section end helical coil.

9. The extendable guidewire system of claim 8 wherein the guidewire section includes a rotating joint contiguous the guidewire section proximal end helical coil.

10. The extendable guidewire systems of claim 9 wherein the rotating joint is a ball and socket joint.

11. The extendable guidewire system of claim 9 wherein the rotating joint is formed by a first coil having spatially separate turns and a second coil having spatially separate turns, with the first and second coil spatially separated turns being adaptable to receive the other spatially separated turns in a winding relationship as the guidewire proximal end helical coil and extension wire end helical coil are being rotated together.

12. The extendable guidewire system of claim 8, wherein the extension wire section includes a cylindrical receiver attached to said extension wire section and extending out from said helical coil.

13. The extendable guidewire system of claim 8 wherein the extension wire section includes a rotating joint contiguous the extension wire section end helical coil.

14. The extendable guidewire system of claim 1 wherein the guidewire section includes a rotating joint contiguous the guidewire section proximal end helical coil.

15. The extendable guidewire system of claim 1 wherein the extension wire section includes a rotating joint contiguous the extension wire section end helical coil.

16. A guidewire extension system, comprising:
    a guidewire having proximal and distal ends;
    an extension wire having opposing ends; and
    first and second flexible connectors associated with one of the extension wire ends and with the guidewire proximal end and including at least partially interlocking helical coil portions;
    wherein said first and second flexible connectors are helical coils having one or more spatially separated coil turns to form gaps for receiving the coil turns of the other connector.

17. An extendable guidewire system comprising:
    A guidewire section designed for placement into a vascular system having proximal and distal ends, the guidewire section proximal end including a helical coil having a free end and spaced apart adjacent coil turns, said guidewire section including a cylindrical receiver attached to said guidewire and extending out from said helical coil; and
    an extension wire with opposing ends with one of such ends including a helical coil having a free end and spaced apart adjacent coil turns, the coil turns of the guidewire proximal end helical coil or the extension wire helical coil being spatially separated so as to receive the coil turns of the other helical coil when the free ends of the guidewire proximal end helical coil and extension end helical coil are rotated into each other, the extension wire helical coil including therewithin a stem, the stem being attached to the extension wire and projecting from the extension wire helical coil to cooperate with the cylindrical receiver to assist positive engagement of the extension and guidewire coils.

18. An extension wire system according to claim 17 wherein the stem projects beyond the free end of the guidewire helical coil.

19. A guidewire system according to claim 17 wherein the cylindrical receiver projects beyond the free end of the guidewire helical coil.

20. A guidewire system according to claim 17 wherein the distance between spaced apart adjacent coil turns of the guidewire coil or the extension wire coil is variable so that rotating one coil into the other provides increasingly tactile positive engagement.

21. The extendable guidewire system of claim 17 wherein the guidewire section includes a rotating joint contiguous the guidewire section proximal end helical coil.

22. The extendable guidewire system of claim 17, wherein the extension wire section includes a rotating joint contiguous the extension wire section end helical coil.

23. A method for connecting an extension wire section to a guidewire section, comprising the steps of:

providing a guidewire section having proximal and distal ends, the guidewire section proximal end including a helical coil having a free end and spaced apart coil turns;

providing an extension wire with opposing ends with one of such ends including a helical coil having a free end and spaced apart adjacent coil turns; and rotating the free ends of the guidewire proximal end helical coil and the extension end helical coil so that the spatially separated coil turns of the guidewire proximal end helical coil receive the coil turns of the extension end helical coil to effect engagement of the coil turns.

24. The method of claim 23, wherein the extension wire helical coil is provided with a guiding pin therewithin, further comprising the step of inserting the guiding pin into the guidewire proximal end helical coil to align the coil turns of the guidewire proximal end helical coil and the extension end helical coil.

25. The method of claim 24, further comprising the step of inserting the guiding pin into a cylindrical receiver provided within the guidewire proximal end helical coil.

* * * * *